US00RE47403E

(19) United States
(12) Reissued Patent
Beyer et al.

(10) Patent Number: US RE47,403 E
(45) Date of Reissued Patent: May 28, 2019

(54) CALIBRATION OF SENSORS OR MEASURING SYSTEMS

(71) Applicant: Roche Diabetes Care, Inc.

(72) Inventors: Uwe Beyer, Bern (CH); Michael Krieftewirth, Ersigen (CH); Ulrich Haueter, Grosshochstetten (CH)

(73) Assignee: Roche Diabetes Care, Inc., Indianapolis, IN (US)

(21) Appl. No.: 14/978,449

(22) Filed: Dec. 22, 2015

Related U.S. Patent Documents

Reissue of:
(64) Patent No.: 8,880,371
Issued: Nov. 4, 2014
Appl. No.: 11/460,160
Filed: Jul. 26, 2006

U.S. Applications:
(63) Continuation of application No. PCT/EP2004/013586, filed on Nov. 30, 2004.

(30) Foreign Application Priority Data

Jan. 27, 2004 (DE) ..... 10 2004 004 031

(51) Int. Cl.
*A61B 5/145* (2006.01)
*A61B 5/1495* (2006.01)
(Continued)

(52) U.S. Cl.
CPC ..... *A61B 5/0031* (2013.01); *A61B 5/14532* (2013.01); *C12Q 1/001* (2013.01); *C12Q 1/006* (2013.01); *G01N 33/5438* (2013.01)

(58) Field of Classification Search
USPC ..... 73/54.06; 702/85, 68, 104; 600/309, 365
See application file for complete search history.

(56) References Cited

U.S. PATENT DOCUMENTS 4,399,426 A * 8/1983 Tan ..... H03M 1/183 341/120
RE31,750 E * 11/1984 Morrow ..... G07C 3/00 340/683
(Continued)

OTHER PUBLICATIONS

Gerritsen et al. ("A percutaneous device as model to study the in vivo performance of implantable amperometric glucose sensors," Journal of Materials Science: Materials in Medicine 12 (2001) pp. 129-134, 2001 Kluwer Academic Publishers).*
(Continued)

*Primary Examiner* — Anjan K Deb
(74) *Attorney, Agent, or Firm* — Dinsmore & Shohl LLP

(57) ABSTRACT

A method for adjusting a sensor, continuous sensor or automatic measuring system in an interstitium including the steps of adjusting the steepness of a measuring curve and a standard offset (standard axis intercept) prior to the use of the sensor, continuous sensor or measuring system, and adapting the offset by a point calibration by using a reference measure or value during the use. The present invention encompasses sensors, continuous sensors or automatic measuring systems calibrated or adjusted in accordance with the method, and in some embodiments, the offset adjusted prior to use is rectified according to the difference between a value determined by the sensor, continuous sensor or measuring system taking into account the standard steepness and the reference value.

14 Claims, 2 Drawing Sheets

(51) Int. Cl.

| | |
|---|---|
| ***G01D 18/00*** | (2006.01) |
| ***A61B 5/00*** | (2006.01) |
| ***G01N 33/543*** | (2006.01) |
| ***C12Q 1/00*** | (2006.01) |

(56) References Cited

U.S. PATENT DOCUMENTS

| | | | | |
|---|---|---|---|---|
| 5,462,879 | A * | 10/1995 | Bentsen | 436/136 |
| 5,497,772 | A * | 3/1996 | Schulman | A61B 5/14865 204/403.09 |
| 5,660,163 | A | 8/1997 | Schulman et al. | |
| 5,695,623 | A * | 12/1997 | Michel et al. | A61B 5/1486 204/403.05 |
| 5,791,344 | A | 8/1998 | Schulman et al. | |
| 6,240,306 | B1 * | 5/2001 | Rohrscheib et al. | 600/316 |
| 6,475,750 | B1 * | 11/2002 | Han | A61B 5/14532 435/14 |
| 6,998,247 | B2 * | 2/2006 | Monfre et al. | 435/14 |
| 2003/0041652 | A1 * | 3/2003 | Spaid | B01L 3/5027 73/54.05 |
| 2003/0130616 | A1 * | 7/2003 | Steil et al. | 604/66 |
| 2005/0027181 | A1 * | 2/2005 | Goode et al. | 600/365 |
| 2005/0192557 | A1 * | 9/2005 | Brauker et al. | 604/503 |
| 2007/0112344 | A1 * | 5/2007 | Keilman | A61B 5/0031 606/41 |

OTHER PUBLICATIONS

Updike et al. ("A subcutaneous glucose sensor with improved longevity, dynamic range, and stability of calibration," Diabetes Care; Feb. 2000; vol. 23, No. 2; pp. 208-214).*

Choleau et al., "Calibration of a subcutaneous amperometric glucose sensor implanted for 7 days in diabetic patients Part 2. Superiority of the one-point calibration method", Biosensors and Bioeletronics, 2002, vol. 17, pp. 647-654.

Choleau et al., "Calibration of a subcutaneous amperometric glucose sensor Part 1. Effect of measurement uncertainties on the determination of sensor sensitivity and background current", Biosensors and Bioeletronics, 2002, vol. 17, pp. 641-646.

Beyer et al., "Recording of subcutaneous glucose dynamics by a viscometric affinity sensor", Diabetologia, 44, 2001, pp. 416-423.

Calisti et al., "Measure of glycosylated hemoglobin", Acta Biomed, 2005, 76, Suppl 3, pp. 59-62.

Search Report for PCT/EP2004/013586 dated Mar. 23, 2005.

Boyne et al., "Timing of Changes in Intersitial and Venous Blood Glucose Measured with a Continuous Subcutaneous Glucose Sensor", Diabetes, vol. 52, pp. 2790-2794, Nov. 2003.

* cited by examiner $$[Glucose] = \underline{gain} \cdot F_r + offset \quad (2)$$

$$F_r = \frac{p_1 - p_2}{p_2 \boxed{+\underline{\alpha} \cdot (p_1 - p_2)}} \quad (1)$$

CALIBRATION OF SENSORS OR MEASURING SYSTEMS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a continuation of International Application No. PCT/EP2004/013586, filed on Nov. 30, 2004, which claims priority to German Application No. 10 2004 004 031.1, filed on Jan. 27, 2004, the contents of which are incorporated in their entirety by reference.

BACKGROUND

The invention relates to devices for delivering, dispensing, injecting or administering substances, to devices for sampling, measuring, testing, sensing or extracting substances, and to methods of making, using, adjusting, setting or calibrating such devices. More particularly, it relates to setting or calibrating such devices, including to a calibration, including a multiple one-point calibration, of an offset in conjunction with a constant gradient of a sensor, in some embodiments, a subcutaneous sensor. One use or application of such sensors relates to glucose measurement with sensors in the interstitium.

Generally, because of instabilities of enzymatic sensors, the gradient of the sensor is calibrated. In a two-point calibration, both the gradient and offset are calibrated, while in a one-point calibration only the gradient is calibrated, the offset being neglected (Choleau et al., Biosensors & Bioelectronics 17 (2003), 647-654).

SUMMARY

It is an object of the present invention to simplify the calibration of a sensor or measuring system, and to provide a sensor and a measuring system comprising the sensor, which sensor or sensor system can be easily calibrated and, in some preferred embodiments, automatically calibrates itself.

The present invention addresses the preceding object by using a sensor or measuring system with a stable gradient in combination with a correction only of the offset of the sensor or measuring system by means of a one-point calibration. The gradient is stable at least over the predetermined duration of use, that is to say it can be regarded as invariable over the duration of use for practical requirements. In some preferred embodiments, the gradient is constant over the measuring range of the sensor, but can also fundamentally be a function that is variable in dependence on the value of a parameter to be measured, but nevertheless be sufficiently stable with reference to the duration of use and changes in the measuring conditions, for example temperature fluctuations. The stability of the gradient permits a simple calibration only with reference to the offset. A sensor operated exactly with reference both to the gradient and to the offset, or an exactly operating measuring system is obtained as a result. The measuring system includes the sensor and further components, for example a reference sensor for the calibration and/or further sensors that can be of the named or other type. To the extent that the terms "measuring sensor" or simply "sensor" is referred to herein, this denotes the sensor for the actual measurement that is to be carried out over a lengthy period, and not a reference sensor used only for the calibration.

In some embodiments, the present invention comprises a method for adjusting a sensor, continuous sensor or automatic measuring system in an interstitium including the steps of adjusting the steepness of a measuring curve and a standard offset (standard axis intercept) prior to the use of the sensor, continuous sensor or measuring system, and adapting the offset by a point calibration by using a reference value measured during the use. The present invention encompasses sensors, continuous sensors or automatic measuring systems calibrated or adjusted in accordance with the method, and in some embodiments, the offset adjusted prior to use is rectified according to the difference between a value measured or determined by the sensor, continuous sensor or measuring system taking into account the standard steepness and the reference value.

In some embodiments, the present invention comprises a method for adjusting sensors, continuous sensors or automatic measuring systems in an interstitium consisting in adjusting the steepness of a measuring curve and a standard offset (standard axis intercept) at a factory prior to the use thereof, in adapting the offset by a point calibration by means of a reference measure during the use. For this purpose, the offset adjusted at the factory is rectified according to the difference between a value determined by the sensor or the measuring system taking into account the standard steepness and the reference value.

In some preferred embodiments, a suitable sensor is the viscosimetric affinity sensor, used for determining the glucose concentration in a body fluid. The viscosimetric affinity sensor for glucose has a linear dependency, stable in the long term, on the glucose concentration and virtually no drift (Beyer et al., Diabetologia (2001) 44, 416-423). Furthermore, it is temperature stable (Beyer et al., Biotechnol. Prog. 2000, 16, 1119-1123). The gradient of the output signal is determined by the glucose characteristic curve of the sensitive liquid and the measuring geometry. The sensor response can already be adapted very precisely, by an external calibration by means of a glucose standard solution, to the actual glucose concentration in physiological fluids, the reliability of the sensor output or measuring system output thereby being enhanced, and a subsequent fine calibration on the basis of, for example, blood glucose concentrations being improved (Beyer et al., Biosensors & Bioelectronics 18 (2003), 1391-1397). The use of viscosimetric affinity sensors is not restricted to the determination of glucose concentration; rather, such sensors have a wide spectrum of use, for which reference may be made, for example, to DE 195 01 159 A1 and to Beyer et al., Lebensmittel- & Biotechnologie 1996/4, 143-146. Preferred viscosimetric affinity sensors and/or measuring systems and methods based thereon are disclosed, for example, in DE 100 10 539 A1, which may be referred to in this regard.

The offset for a sensor of fixed gradient can, for example, be automatically determined and corrected by comparing the mean for 24 hours or a number of days with the long-term value that is calculated from the values for the glycosylated hemoglobin, that is to say Hb A1 or Hb A1c. Such a person-specific calibration can already be sufficient for an in-vivo measurement of the glucose concentration with the measuring sensor. Making use in a supplementary fashion or even exclusively of a long-term reference value for the sensor calibration is advantageous not only for the inventive correction of the offset, but basically also for other types of calibration, for example a two-point calibration for correcting the gradient of less stable sensors and of the offset, or else a one-point calibration for correcting the gradient.

Instead of, or else in addition to the above-named correction on the basis of a long-term reference value, it is possible to carry out a reference measurement with a reference unit that measures in the capillary blood, for example at the finger pulp or the forearm, or in the blood plasma. In some preferred embodiments, the reference measurement in the capillary blood is preferred.

In some preferred designs or embodiments of the present invention, the sensor or the measuring system is adapted by the calibration with reference to physiological circumstances on which a subcutaneous measuring system is based and that result from the compartment error, caused by the reference measurement in the capillary blood or blood plasma and the arrangement of the measuring sensor in the subcutaneous tissue. The deviations between the various compartments comprise a phase shift in the case of the rise in glucose in the blood by comparison with the tissue, and also a lesser amplitude in the tissue by comparison with the blood. Taking account of the time shift can greatly improve the accuracy of the adaptation of a sensor system or measuring system. The calibration can either be performed such that an operator or the measuring system calibrates independently in an automatic fashion at one or more instants at which there is no strong dynamics in the glucose signal, or the trend is taken into account, specifically the first derivative of the filtered glucose signal, which is used to take account of the suitable time shift between the reference measurement and the sensor signal. This time shift depends on phase and has been described by Lönnroth in a model. In advantageous designs, the trend, which is calculated, in some preferred embodiments, continuously, by the measuring system or the reference unit automatically and during the measurement, is used to determine a favorable instant for the calibration by virtue of the fact that a phase of low dynamics is identified with the aid of the calculated trend values, and the calibration is carried out with the aid of a reference value and a measured value from the corresponding time interval. For the automatic calculation of trends, a data acquisition device of the measuring system has a memory in which the data used for calculating the trend values are stored, the data being assigned the respective measuring time. The calculation of the trend is advantageous not only in connection with the correction of the offset by the one-point calibration, but also generally in connection with other methods of calibration and measuring systems operating in accordance therewith.

The reference unit can be a component of the measuring system, or can be used, in a fashion detached from an individual measuring system, as a standard unit for a relatively large number of inventive measuring systems. In designs or embodiments in which the reference unit belongs to the measuring system, it can correspond at least to the type according to the measuring sensor.

The reference value can simply be the value, obtained from a single measurement, of a single reference unit. However, it can advantageously also be formed as the mean of two reference values that are obtained by means of the type according to different reference units, or from measurements at different locations, in each case on the same person or, quite generally, on the same measurement object. The reference value can directly be a value of the parameter to be measured, for example the glucose concentration. However, it can also be a value of another variable, for example a physical variable such as pressure from which, in this case, the parameter is first formed, either in the reference unit or by the data acquisition device for the measuring sensor.

In some preferred embodiments, the measuring sensor or the measuring system including the measuring sensor is suitable for the self-administration of insulin or another drug or preparation, such as a liquid product or substance. In such preferred uses, the in-vivo measurement can advantageously likewise be carried out by the person administering the product to himself. In one development of the present invention, the same person can also carry out the reference measurement or, if appropriate, the several reference measurements himself.

In some embodiments, the measuring system executes the measurement continuously without interruptions to the measurement operation, or sequentially over time. During the measurement operation, the sensor periodically outputs, in some instances, at specific time intervals, a measuring sensor value or a set of measuring sensor values respectively assigned to the same state, which value(s) is/are processed in a data acquisition device of the measuring system and is/are at least buffered. In the case of the measurement sequentially over time, the measurement periods can be preset by the manufacturer or, for example, an attending doctor, or be set by the user himself. Also conceivable is measurement at measurement periods that can be flexibly determined, that is to say measurement respectively at the behest of the user. It can be advantageous to measure only sequentially over time, for example to save energy, or, in the case of a measuring system based on the conveyance of a sensitive liquid, to keep the quantity of the liquid to be conveyed slight.

Although the use of only a single one-point calibration already suffices to adapt the sensor or the measuring system for a lengthy measuring period to the individual physiology of a person, of an animal or, quite generally, to the influences specific to a particular measurement object, a multiple one-point calibration is carried out, that is to say the sensor or the measuring system is calibrated over the measuring period in accordance with the present invention, for example once per day, once for a number of days or, even several times per day. Again, updating the calibration can be performed by means of a reference unit by a person who executes the measurement on himself. The relevant person need only, as previously customary in diabetes therapy, for example, perform on himself measurements that now, however, serve as reference measurements for the calibration and expedient monitoring of the system. In some embodiments, if the relevant reference unit is connected to the data acquisition device of the inventive system in a wired fashion or in a wireless fashion by radio, IR radiation or another transmission technique, the inventive calibration is performed automatically on the basis of the respective reference measurement such that no manual interventions are required beyond those required to carry out the reference measurement or, if appropriate, the confirmation that calibration is to be performed.

In some preferred embodiments, the data acquisition device of the measuring system has an integrated display device, for example an optical display, a speech output or an alarm, to display or to submit to the user the current value of the monitored parameter, advantageously its historical profile, risk situations and, if appropriate, handling proposals as well.

Some preferred embodiments of the present invention may comprise direct or indirect transmission of reference data of a reference unit to a monitor, to a monitor and a data acquisition device associated with a measuring system, or only to a data acquisition device of a measuring system. In any embodiment, transmission of data may be accomplished in a suitable manner, e.g., in a wireless or wired fashion.

DETAILED DESCRIPTION OF THE DRAWINGS

Figure 1:
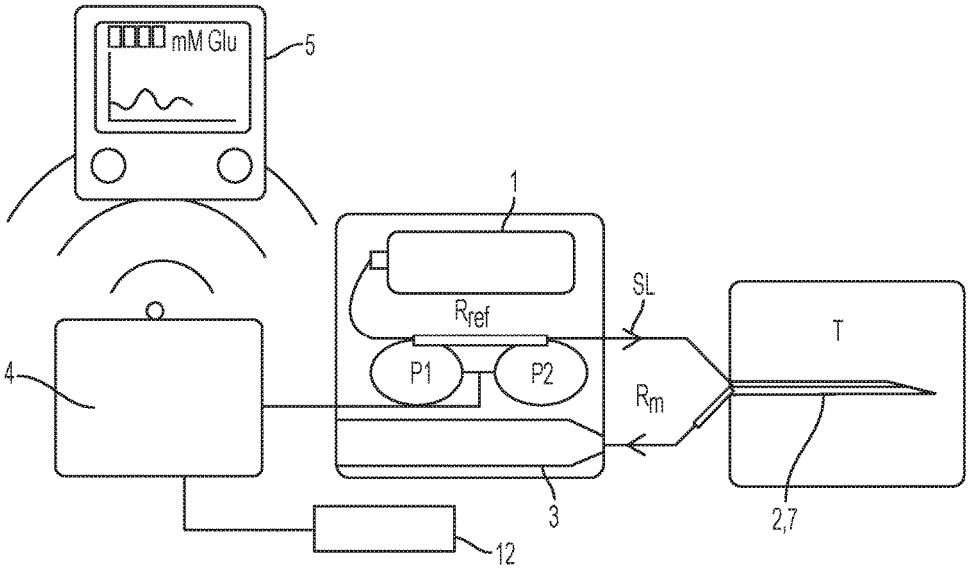
FIG. 1 shows an exemplary measuring system.

FIG. 1 shows a measuring system having a dialysis probe 2 that is introduced subcutaneously in body tissue T. A sensitive liquid SL whose viscosity changes as free glucose is absorbed flows continuously through the probe. A hydraulic reference resistance $R_{ref}$ is arranged upstream of a dialysis chamber 7 of the dialysis probe 2 in the flow path of the sensitive liquid SL, and a hydraulic measuring resistance $R_m$ is arranged downstream of the dialysis chamber 7. A pressure sensor for measuring a pressure P1 is arranged upstream of the reference resistance $R_{ref}$, and a further pressure sensor for measuring a pressure P2 is arranged downstream of the reference resistance $R_{ref}$ and still upstream of the dialysis chamber 7. The two pressures P1 and P2 are measured as differential pressures relative to the ambient pressure. The sensors are therefore differential-pressure sensors. Furthermore, the measuring system comprises a data acquisition device 4 and a monitor 5 that is connected in a wireless fashion, for example by infrared radiation or by radio, to the data acquisition device 4. The monitor 5 can be, for example, the monitor of a PC or of an infusion unit such as are known as units that can be worn on the body, for example those from diabetes therapy. Instead of this, or in addition, such a monitor can also be an integrated constituent of the measuring system, that is to say be integrated in a housing that accommodates the data acquisition device 4 and, if appropriate, also further components of the measuring system, for example a pump 1 and/or a disposal container 3.

Figure 2:
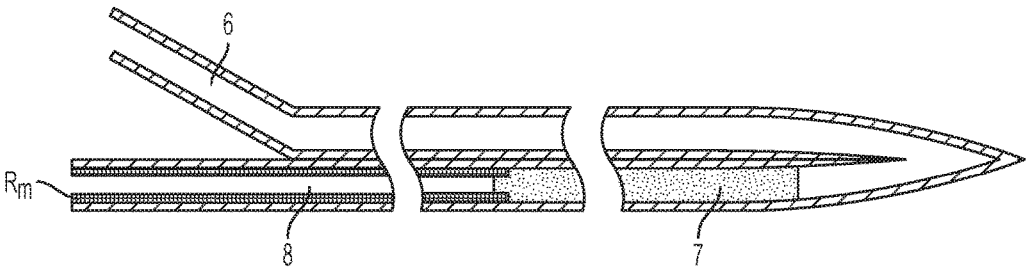
FIG. 2 shows an exemplary dialysis probe.

FIG. 2 shows the dialysis probe 2 in an enlarged fashion. An inlet tube for the sensitive liquid is marked with the reference numeral 6, and an outlet tube is marked with the reference numeral 8. Between the inlet tube 6 and the outlet tube 8, the sensitive liquid flows through a dialysis fiber or a dialysis fiber bundle that forms or helps to form the dialysis chamber 7, and serves to hold the glucose. The measuring resistance $R_m$ is arranged in the outlet tube 8.

For the purpose of glucose measurement, the sensitive liquid SL is conveyed by the pump 1 via the reference resistance $R_{ref}$ to the dialysis probe 2, flows through the dialysis chamber or dialysis fiber thereof and, subsequently, the measuring resistance $R_m$ before the liquid enriched with glucose in the dialysis chamber 7 reaches the disposal container 3. The sensitive liquid flows continuously. By means of the pressure sensors, the two differential pressures P1 and P2 are continuously measured and transmitted to the data acquisition device 4 by wire or in a wireless fashion. The data acquisition device 4 calculates the glucose concentration therefrom.

Figure 3:
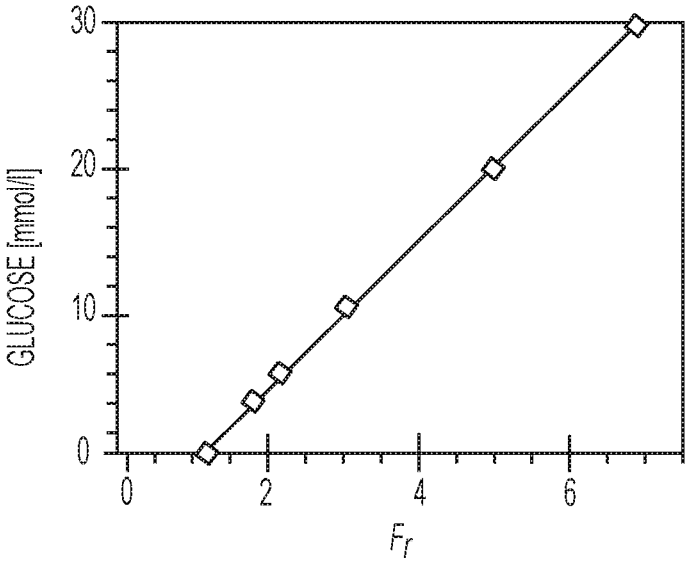
FIG. 3 shows glucose concentration as a function of the relative fluidity.

FIG. 3 shows the relationship between the so-called relative fluidity $F_r$ and the glucose concentration. The relative fluidity $F_r$ is calculated, using the formula specified in FIG. 3, from the two pressures P1 and P2 with the aid of a constant $\alpha$ that is a linearization parameter dependent on the sensitive liquid and the ratio of the resistances $R_m$ and $R_{ref}$:

$$F_r=(P1-P2)/(P2+\alpha(P1-P2)) \quad (1).$$

For further details relating to the relative fluidity and the relationship to the glucose concentration, reference may be made to DE 100 10 539 A1 and, furthermore, to Beyer et al., 2000 and 2001. As FIG. 3 shows, the glucose concentration is yielded by means of linear regression as:

$$[\text{Glucose}]=\text{gain}*F_r+\text{offset} \quad (2).$$

"Gain" denotes the slope or gradient with which the glucose concentration increases as a function of the relative fluidity $F_r$.

The data acquisition device 4 is programmed and can, if appropriate, also be programmed individually by the user, and calculates the glucose concentration from the transmitted data pair P1 and P2 and the permanently stored linearization coefficient $\alpha$, doing so at prescribed or selected time intervals, in some preferred embodiments, periodically, for example every six seconds. The calculated values of the glucose concentration are stored in a memory of the data acquisition device 4 in accordance with the time profile.

Furthermore, the data acquisition device 4 uses the stored values of the glucose concentration to calculate the trend, that is to say the speed at which the glucose concentration varies, specifically from values of the glucose concentration that had been determined in an interval of a few minutes, for example three minutes. In terms of software, the data acquisition device 4 has a subroutine for calculating the first derivative of the glucose concentration [glucose] with respect to the measuring time t. The data acquisition device 4 compares the trend function d[glucose](t)/dt, specifically their numerical approximation, with a comparison value. If the calculated trend value undershoots the comparison value in absolute magnitude, the data acquisition device 4 deduces a low level dynamics of the glucose concentration, and thus a favorable point in time for calibrating the measuring system. If a favorable point in time is identified, the data acquisition device 4 alerts the user to this so that he executes a reference measurement, e.g., in the capillary blood, with the aid of a reference unit. The reference value determined from the reference measurement by the reference unit is automatically sent by the reference unit and received by the data acquisition device 4 which, thereupon, automatically executes a calibration by correcting the offset with the aid of a one-point calibration. Mathematically, during the calibration only the value of the offset is varied, that is to say the regression line is displaced in parallel such that the difference between the value of the glucose concentration determined from the measurement, and the value of the glucose concentration determined from the reference measurement is reduced and/or, in some preferred embodiments, made to vanish. If the reference unit already calculates the glucose concentration of the reference measurement from the recorded reference variable and transmits it as reference value, the data acquisition device 4 can immediately perform the comparison of reference value and characteristic value, that is to say the glucose concentration calculated in accordance with formulas (1) and (2), and perform the calibration directly thereupon. However, if the reference unit transmits the value of the recorded reference variable only directly, the data acquisition device 4 is advantageously equipped, and/or appropriately programmed, with the ability to calculate the glucose concentration of the reference measurement from the reference value. If a number of reference measurements are carried out to increase the reliability of the calibration, if appropriate with the aid of different reference units, the data acquisition device 4 advantageously also has the ability to form the mean via the reference values, of which there are then several, and to carry out calibration on the basis of the mean.

The measuring system can be fitted with an input device 12, for example a keyboard or voice data entry or a touch screen, to input reference value(s) manually. Such an input device can also be used to input a value for the glycosylated hemoglobin. In some preferred embodiments, to correct the offset on the basis of such a long-term value, the data acquisition device 4 has the programmed ability to average the values of the glucose concentration, determined from the measurement, over a day or else several days, and to compare the glucose concentration mean over one or several days with the long-term value.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A measuring system for determining a value of a glucose concentration, the measuring system comprising:

a. a measuring sensor (2, $R_m$, $R_{ref}$), having a known gradient and a known offset, for recording a measured value in vivo in a temporally sequential or continuous fashion, and outputting measuring sensor values (P1, P2), the measured values of the measured variable or formed from the measured values, and b. a data acquisition device that receives the measuring sensor values and at least one reference value and forms characteristic values of the glucose concentration from the measuring sensor values, wherein the measuring sensor is a glycose sensor and the at least one reference value is a long-term glycose value, and wherein the data acquisition device creates a long-term glucose value from the at least one reference value and calculates a daily mean or a multiple daily mean of the glucose concentration from the measuring sensor values, and the offset is corrected in accordance with the result of the comparison of the daily mean or multiple daily mean with the long-term glucose value to minimize the difference between the daily mean or multiple daily mean and the long-term glucose value; and wherein c. for the purpose of an automatic self-calibration of the measuring system, the data acquisition device compares the at least one reference value or a value calculated therefrom with the characteristic value from the corresponding time interval, and the offset of the measuring sensor is adjusted in accordance with the result of the comparison by a one-point calibration.

2. The measuring system as claimed in claim 1, wherein the measuring sensor comprises a dialysis probe.

3. The measuring system as claimed in claim 1, wherein the measuring sensor comprises a probe that can be placed in a body and a conveyor device by which a liquid can be conveyed through, only into or only out of the probe.

4. The measuring system as claimed in claim 1, wherein the measuring sensor comprises a flow resistance zone [($R_{re}$f)] ($R_{ref}$) and the measured variable recorded by the measuring sensor is a pressure of a fluid flowing through the flow resistance zone.

5. The measuring system according to claim 4, wherein the flow resistance zone comprises a flow resistance capillary.

6. The measuring system as claimed in claim 4, wherein a pressure is measured at an upstream inlet and a downstream outlet of the flow resistance zone ($R_{ref}$), and the pressure values are transmitted to the data acquisition device.

7. The measuring system as claimed in claim 1, wherein the measuring sensor comprises a dialysis chamber through which a sensitive liquid can flow, a flow resistance zone arranged upstream of the dialysis chamber, a flow resistance zone arranged downstream of the dialysis chamber, a pressure transmitter upstream of one of the flow resistance zones, and a pressure transmitter downstream of that one of the flow resistance zones, one of the pressure transmitters being arranged between the flow resistance zones, wherein pressure values recorded by the pressure transmitters are transmitted to the data acquisition device.

8. The measuring system as claimed in claim 7, wherein the data acquisition device calculates from the pressure values a relative fluidity $F_r$ using $$F_r=(P1-P2)/(P2+\alpha(P[1]2-P2)),$$

P1 being the pressure value of the upstream pressure transmitter, P2 being the pressure value of the downstream pressure transmitter and [a] $\alpha$ being a linearization coefficient.

9. The measuring system as claimed in claim 8, the data acquisition device calculates a concentration of a substance in a fluid from the relative fluidity $F_r$ by using the formula $$[KONZ]=gain*F_r+offset.$$

10. The measuring system as claimed in claim 9, wherein the data acquisition device calculates a trend using measuring sensor values, and determines an instant for the calibration from the calculated trend.

11. The measuring system as claimed in claim 1, wherein the data acquisition unit comprises a data memory for a number of the measuring sensor values, and a clock to assign the measuring sensor values the respective instant of their recording.

12. The measuring system as claimed in claim 1 further comprising a reference unit for recording the measured variable or another measured variable, and for outputting the at least one reference value determined from the measured variable or the other measured variable.

13. The measuring system as claimed in claim 12, wherein the reference unit automatically transmits the at least one reference value to the data acquisition device in a wireless fashion or by wire per data transmission.

14. A measuring system for determining a value of a glucose concentration, the measuring system comprising:

a. a measuring sensor (2, $R_m$, $R_{ref}$), having a known gradient and a known offset, for recording a measured value in vivo in a temporally sequential or continuous fashion, and outputting measuring sensor values (P1, P2), the measured values of the measured variable or formed from the measured values, wherein the measuring sensor is a viscosimetric affinity sensor, and b. a data acquisition device that receives the measuring sensor values and at least one reference value and forms characteristic values of the glucose concentration from the measuring sensor values, wherein the measuring sensor is a glycose sensor and the at least one reference value is a long-term glycose value, and wherein the data acquisition device creates a long-term glucose value from the at least one reference value and calculates a daily mean or a multiple daily mean of the glucose concentration from the measuring sensor values, and the offset is corrected in accordance with the result of the comparison of the daily mean or multiple daily mean with the long-term glucose value to minimize the difference between the daily mean or multiple daily mean and the long-term glucose value; and wherein c. for the purpose of an automatic self-calibration of the measuring system, the data acquisition device compares one of the characteristic values with the at least one reference value or a value calculated therefrom with the characteristic value from the corresponding time interval, and the offset of the measuring sensor is adjusted in accordance with the result of the comparison by a one-point calibration.

* * * * *